United States Patent [19]

Moss et al.

[11] Patent Number: 5,550,035
[45] Date of Patent: *Aug. 27, 1996

[54] PROKARYOTIC EXPRESSION IN EUKARYOTIC CELLS

[75] Inventors: Bernard Moss, Bethesda, Md.; F. William Studier, Stony Brook, N.Y.; Thomas R. Fuerst, Gaithersburg, Md.; Edward G. Niles, Amherst, N.Y.

[73] Assignee: The Research Foundation of State University of New York, Buffalo, N.Y.

[ * ] Notice: The term of this patent shall not extend beyond the expiration date of Pat. No. 5,126,251.

[21] Appl. No.: 187,119

[22] Filed: Jan. 26, 1994

Related U.S. Application Data

[63] Continuation of Ser. No. 648,971, Jan. 31, 1991, abandoned, which is a continuation-in-part of Ser. No. 582,489, Sep. 14, 1990, abandoned, which is a continuation-in-part of Ser. No. 905,253, Sep. 8, 1986, abandoned.

[51] Int. Cl.$^6$ ............................. C12N 5/10; C12N 15/09; C12N 7/01
[52] U.S. Cl. .................... 435/69.1; 435/69.3; 435/172.3; 435/193; 435/207; 435/235.1; 435/240.2; 435/240.4
[58] Field of Search ................... 435/69.1, 172.3, 435/240.2, 320.1, 69.3, 193, 207, 235.1, 240.4

[56] References Cited

U.S. PATENT DOCUMENTS 5,126,251 6/1992 Moss et al. ............................ 435/69.1

*Primary Examiner*—Mindy Fleisher
*Assistant Examiner*—Philip W. Carter
*Attorney, Agent, or Firm*—Nixon, Hargrave, Devans & Doyle

[57] ABSTRACT

A transient expression system is disclosed that utilizes bacteriophage RNA polymerase in the presence of a DNA-based cytoplasmic virus to facilitate expression of a foreign gene in the cytoplasm of a eukaryotic cell.

A method of expressing a foreign gene in the cytoplasm of a eukaryotic cell is also disclosed which comprises incorporating into the cytoplasm a DNA-based cytoplasmic virus, a suitable carrier comprising a gene for an RNA polymerase which gene is foreign to the carrier and to the cells, and a suitable carrier comprising a functional, cistron including a foreign gene flanked by a promotor sequence which is recognized by the RNA polymerase.

43 Claims, 6 Drawing Sheets

PROKARYOTIC EXPRESSION IN EUKARYOTIC CELLS

This invention was made wholly or in part with funds provided by the U.S. Government. The U.S. Government has certain rights in this invention.

This application is a "continuation" of application Ser. No. 07/648,971, filed Jan. 31, 1991, now abandoned, which is a continuation-in-part of Ser. No. 07/582,489, filed Sep. 14, 1990, now abandoned, which is a continuation-in-part of Ser. No. 905,253 filed Sep. 8, 1986, now abandoned.

FIELD OF THE INVENTION

This invention relates generally to the expression of genes in a eukaryptic environment and more particularly, to a transient expression system that utilizes bacteriophage RNA polymerase in the presence of a DNA-based cytoplasmic virus to facilitate expression of the gene in the cytoplasm of the eukaroytic cell.

BACKGROUND OF THE INVENTION

Since the inception of microbiology and genetic engineering, there has been a desire to be able to transfer traits from one organism to another.

Recombinant DNA technology has made it possible to develop molecular cloning vectors that allow expression of heterologous genes in prokaryotic cells (cells of lower life forms without a nucleus) and eukaryotic cells (cells of higher organisms). Bacterial systems provide important advantages such as ease of use and high expression but impose a number of limitations for synthesis of eukaryotic proteins. In particular, correct folding, proteolytic processing, glycosylation, secretion, and subunit assembly may not occur or may occur incorrectly in bacteria. For these and other reasons, eukaryotic cells are preferred for expression of eukaryotic genes.

It has also been difficult to obtain expression of certain genes, especially those of lower organisms in cells of higher organisms. This has been true for many reasons including the fact that gene control mechanisms are often significantly different.

It has been known that T7 and certain other bacteriophage RNA polymerases, for example SP6, GH1 and T3, are single subunit enzymes with high catalytic activity and strict promoter specificity, which have found wide application for in vitro synthesis of RNA and as the basis for high-level gene expression systems in *Escherichia coli*. One potential problem with use of a prokaryotic RNA polymerase in a eukaryotic cell, however, is the requirement for mRNA to be processed, capped, methylated, and polyadenylated. Another potential problem concerns the observation that eukaryotic RNA polymerases are produced in the cytoplasm but are transported and subsequently localized in the nucleus. A system using T7 or other bacteriophage RNA polymerases would require localization of the enzyme in the cytoplasm to act on foreign genes contained within the vector also localized in the cytoplasm. Therefore, a transient system which could utilize the advantages of a bacteriophage RNA polymerase, which could function in an eukaryotic environment to facilitate the expression of a foreign gene, and which is simple, widely applicable, and highly efficient, is desirable.

SUMMARY OF THE INVENTION

In accordance with the present invention, it has been discovered that foreign genes encoding a single subunit RNA polymerase can be used in eukaryotic cells when the procedures and vectors of the present invention are employed.

In particular, the invention comprises a method of expressing a foreign gene in the cytoplasm of a eukaryotic environment comprising living eukaryotic cells. The method comprises incorporating a DNA-based cytoplasmic virus into the evironment along with a suitable carrier i.e. vector, encoding a single subunit RNA polymerase which is foreign to the carrier and to the cells, along with a suitable carrier comprising a functional cistron including a promoter responsive to the bacteriophage RNA polymerase. The cistron further includes the gene to be expressed and may include a phage RNA polymerase specific transcription termination sequence.

The vector and DNA-based cytoplasmic virus may be the same, and it is within the scope of the present invention to include novel DNA-based cytoplasmic viral vectors. A combined vector may include a DNA-based cytoplasmic virus containing a foreign gene encoding for a functional specific single subunit RNA polymerase and a DNA-based cytoplasmic virus comprising a functional cistron including a foreign gene sequence flanked by a bacteriophage promotor and perhaps a termination sequence which functions with the bacteriophage RNA polymerase.

More particularly, one embodiment of the present invention may comprise a vaccinia/T7 transient expression system. This illustrative system is designed for expression of a foreign gene. The foreign gene is inserted into a vector between bacteriophage RNA polymerase T7 promoter and terminator sequences. Expression of the gene is facilitated by another vector encoding a bacteriophage RNA polymerase i.e., T7, polymerase which very specifically initiates transcription of DNA to m-RNA and eventual production of foreign protein. The foreign genes expressed utilizing this illustrative system includes the HBsAg gene of hepatitis B Virus (HBV) and the prokaryotic genes lacZ and CAT.

DETAILED DESCRIPTION OF THE INVENTION

Figure 1:
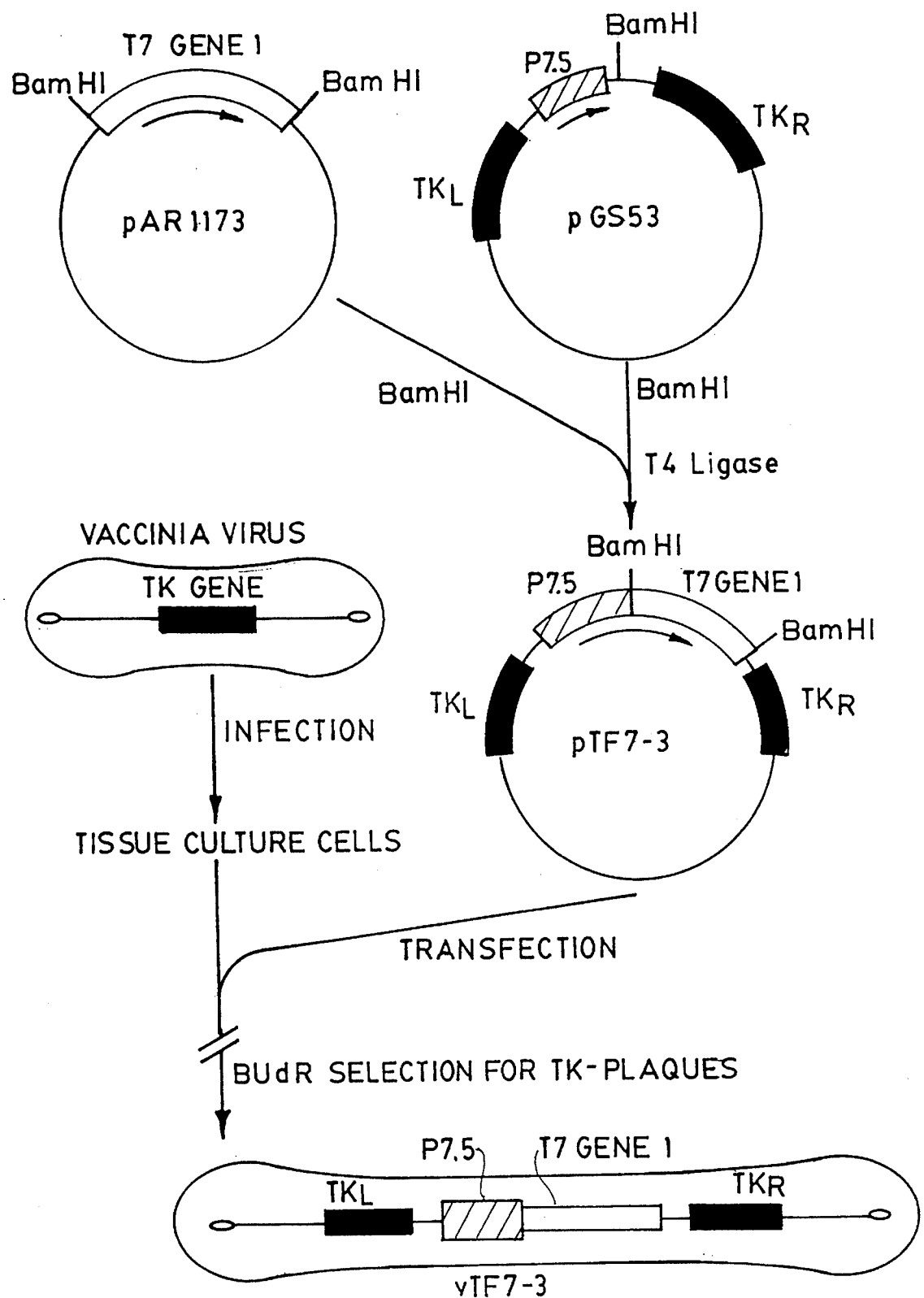
FIG. 1 is a schematic diagram showing insertion of bacteriophage T7 gene 1 which encodes RNA polymerase into the genome of vaccinia virus. A 2.65 Kb BamHI fragment containing T7 gene 1 was excised from pAR1173 and inserted into the unique BamHI site of pGS53 to form pTF7-3. In the latter plasmid, the coding sequence for T7 RNA polymerase is downstream of the vaccinia P7.5 promoter and the chimeric gene is flanked by the left (TKL) and right (TKR) vaccinia TK sequences. DNA segments are not drawn to scale. CV-1 cells were infected with vaccinia virus and transfected with pTF7-3. After 48 hrs, the cells were harvested and the virus was plaqued on TK- cells in the presence of BUdR. Virus plaques were amplified and screened by dot blot hybridization to T7 gene 1 DNA.

In accordance with the present invention, a transient expression system has been discovered which for the first time utilizes highly efficient single subunit bacteriophage RNA polymerases, such as those from T7, SP6, GH1, and T3 viruses, in a eukaryotic environment. As previously discussed, the use of such RNA polymerases in eukaryotic environments has not been practical or possible due to supplemental requirements associated with expression of genes by such RNA polymerases. In accordance with the present invention, it has been discovered that the presence of a DNA based cytoplasmic virus will permit such a gene to be expressed in a eukaryotic environment.

The term "DNA-based cytoplasmic viruses", as used herein, are viruses that contain genetic material made up of DNA (versus an RNA virus) that when infecting a cell carries its genetic material into the cytoplasm of the target cell.

The DNA-based cytoplasmic viruses lack proper signals or apparatus to enter the nucleus of the infected cell, but contain all necesary information for transcription and replication in the cytoplasm, and thus provide some of the necessary components that contribute to expression of a foreign gene.

The major family of viruses which transcribe and replicate their DNA in the cytoplasm are the poxviruses; although certain Iridoviruses, such as swine fever virus, often transcribe and replicate much of their DNA in the cytoplasm and therefore may be used in accordance with the present invention.

Examples of genera of poxviruses within the scope of the present invention include orthopoxvirus, parapixvirus, avipoxvirus, capripoxvirus, leporipoxvirus, suipoxvirus molluscipoxvirus and yatapoxvirus. More particlarly, examples of species of poxviruses within the scope of the present invention include rabbit pox virus, cow pox virus, shope fibroma virus, ectomelia (mouse pox virus), and vaccinia virus. Vaccinia virus is especially suitable for use in accordance with the present invention and further detailed discussion will refer to this virus. It is, however, to be understood that such a discussion in general similarly applies to the other cytoplasmic DNA viruses.

Vaccinia virus, the prototypal member of the poxvirus family, has a large linear double-stranded DNA genome that encodes an entire transcription system including RNA polymerase, capping/methylating enzymes, and poly(A) polymerase. Additional advantages of vaccinia virus include its large capacity for foreign DNA, genome stability, and wide vertebrate host range. These characteristics have been utilized in the development of vaccinia virus as a eukaryotic expression vector.

The RNA polymerase genes which may be used in accordance with the present invention include any RNA polymerase which will function in the cytoplasm of a eukaryotic cell in the presence of a DNA-based cytoplasm virus. For purposes of example, particularly suitable are RNA polymerase genes from bacteriophage, bacterial viruses, and especially the T7, SP6, GH1, and T3 viruses. For purposes of illustrating a preferred embodiment of the present invention, and not limitation, the T7 RNA polymerase gene will be discussed in detail. The T7 RNA polymerase gene is isolated from the prokaryotic (viral) T7 bacteriophage. The T7 bacteriophage infects bacteria, but not eukaryotic cells. The T7 RNA polymerase is highly specific for promotor sequences contained within the bacteriophage genome. Accordingly, it is understood that the chances of finding a similar sequence in eukaryotic or other DNA are very nominal. For a further discussion on the specificity and individual promotors recognized by the bacteriophage RNA polymerases see Chamberlin et al, *The Enzymes*, vol. 15, pp. 82–108 (1982); and Dunn et al, *J. Mol. Biol.* 166, pp. 477–535 (1983). It is understood that the discussion with respect to the T7 RNA polymerase generally applies to other RNA polymerases, especially the bacteriophage RNA polymerases mentioned above.

The foreign gene which is to be expressed in the eukaryotic environment may be almost any gene sequence. The gene must, however, be included, within a cistron that will function with the bacteriophage RNA polymerase as previously described. "Cistron", as used herein, is a gene including a transcription promoter sequence which permits the gene to be expressed. Optionally, the "cistron may include a termination sequence. As used herein, a "cistron" and a "functional genetic sequence" may be considered the same. Such a cistron therefore includes a promoter, an intermediate or foreign sequence, and may optimally have a termination sequence. The intermediate or foreign sequence may contain one or more genetic sequences or a plurality of codes encoding polypeptides including proteins from the transcribed corresponding m-RNA. For purposes of describing such an intermediate sequence ehch such individual code will be referred to herein as a "gene." The promoter of the cistron used in accordance with the present invention functions with the RNA polymerase, as previously described. A further detailed discussion will be directed to such cistrons beginning with a T7 promoter. However, it is understood that such a discussion is for purposes of illustration only and, not limitation. For example, other promoters which will function with a T7 RNA polymerase or with other bacteriophage RNA polymerases are within the scope of the present invention.

The carrier used to deliver the gene for the RNA polymerase or the cistron into the eukaryotic environment includes any suitable vector, such as a plasmid or a virus. It is understood that the terms "vector" and "carrier", as used herein, are intended to be interchangeable terms. In accordance with the present invention, a DNA-based cytoplasmic virus in the eukaryotic environment permits the RNA polymerase gene to be expressed. The same virus may also act as a vector in accordance with the present invention, i.e. it may also be used to introduce the RNA polymerase gene or the cistron into the environment. Optionally a plasmid may be used as the vector or vectors to introduce the RNA polymerase gene and/or the cistron into the eukaryotic environment. When using a plasmid as the carrier of the foreign gene, a DNA-based cytoplasmic virus is needed to provide information required for expression of the RNA polymerase gene. The cytoplasmic DNA virus may also provide other functions including capping and polyadenalation of the RNA synthesized by the T7 RNA polymerase.

A better understanding of the present invention and of its many advantages will be had by referring to the following examples. It is understood however, that the procedures and examples described hereinafter are for purposes of illustration only, and that any changes or modifications which suggest themselves to one of ordinary skill in the art are within the scope of the present invention.

EXAMPLE I

Materials and Methods 1.0 ENZYMES

For the procedures described, enzymes were supplied by the companies indicated and used in accordance with their instructions. Restriction endonucleases were from Bethesda Research Laboratories, New England BioLabs or Boehringer Mannheim Biochemicals. The Klenow fragment of DNA polymerase I and T4 DNA ligase were from New England BioLabs. Calf intestinal alkaline phosphatase was obtained from Boehringer Mannheim Biochemicals.

2.0 VIRUS AND CELLS

Vaccinia virus (strain WR) was originally obtained from the American Type Culture Collection, replicated in HeLa cells, and purified per the procedure of Mackett et al., *DNA Cloning*, Vol. 2, pp. 191–211, 1985. HeLa cells were grown in Eagle's medium supplemented with 5% horse serum. Human TK- 143 cells (Rhine et al., Int. J. Cancer, 1975, 15, pp 23–29) were grown in Eagle's medium with 10% fetal bovine serum (FBS) and 25 µg of 5-bromodeoxyuridine (BUdR) per ml. CV-1 monkey kidney cells were grown in Dulbecco's modified medium containing 10% FBS.

3.0 PLASMIDS

Plasmid pGS53 contains the vaccinia virus P7.5 promoter, unique BamHI and SmaI restriction sites for insertion of foreign genes, and thymidine kinase (TK) flanking sequences. It differs from the pGS20 vector, (Mackett et al., J. Virol, 1984, 49 pp 857–864), principally in the use of pUC13 plasmid (Messing, Methods Enzymol., 1983, 101C, pp 20–78) instead of pBR328 and TK flanking sequences derived from the Wyeth strain of vaccinia virus instead of the WR strain.

4.0 Preparation and Cloning of DNA

Recombinant plasmids were constructed and used to transform bacteria following the methods of Maniatis et al., Molecular Cloning, 1982. plasmids were prepared by the alkaline NaDodSO4 method as described by Birnboim and Doly, Nucleic Acids Res., 7, pp 1513–1523, and purified by CsCl/ethidium bromide equilibrium density gradient centrifugation. Plasmids were routinely checked by agarose gel electrophoresis to ensure that the majority of DNA was in the supercoiled configuration. DNA fragments were isolated from low-melting point agarose gels following the Elutip d (Schleicher and Schuell) method. DNA was extracted from purified virus as described in Mackett et al., 1. supra.

5.0 Isolation of Recombinant Virus

To isolate recombinant virus, CV-1 cells were infected with 0.05 plaque forming units (PFU) per cell of wild-type vaccinia virus and transfected with calcium phosphate precipitated plasmid as described previously, Mackett et al., 1. supra. TK$^-$ recombinant virus plaques were isolated on TK$^-$ 143 cell monolayers in the presence of BUdR (25 µg/ml). Recombinant virus plaques were distinguished from spontaneous TK- mutant virus by DNA:DNA dot blot hybridization. After two consecutive plaque purifications, recombinant virus was amplified by infecting TK$^-$ 143 cell monolayers in the presence of BUdR and then large stocks were made in HeLa cells without selection.

6.0 Transient Assay Conditions

For standard assays (Cochran et al., Proc. Nat. Acad. Sci., 1985, 82 pp 19–23) CV-1 cells were grown to 80% confluency in 25 cm2 flasks (approximately $2.5 \times 10^6$ cells) and infected with either purified wild-type of recombinant vaccinia virus at a multiplicity of 30 PFU per cell. The virus was allowed to absorb for 30 minutes at 37° C. with occasional rocking of the plate. The inoculum was then removed and 1 ml of calcium phosphate-precipitated DNA (10 µg of recombinant plasmid and 10 µg of salmon sperm DNA) was added. After 30 minutes at room temperature, fresh medium containing 2.5% FBS was added and the flask was incubated at 37° C. Cells were harvested at 24 hours after infection and suspended in the indicated buffer.

When specified, care was taken to follow the transient expression conditions described by Gorman and co-workers, *Mol. Cell. Biol.* 1982, 2 pp 1044–1051. On the day prior to transfection, low passage number (less than 10 passages) CV-1 cells were plated at a density of $2.5 \times 10^6$ cells per 25 cm$^2$ flask and were refed with Fresh medium containing 10% FBS at 3 hours before transfection. A 2 minute glycerol shock was performed at 3.5 hours after transfection and cell lysates were prepared at 48 hours.

7.0 T7 RNA Polymerase Assay

Approximately $2.5 \times 10^6$ transfected or infected CV-1 cells were resuspended in 0.25 ml of 0.01M Tris-HCl (pH 7.6)/0.01M NaCl/1.5 mM mgCl$_2$ and Dounce homogenized. After centrifugation, 1.5 µl of cytoplasmic supernatant was assayed for T7 RNA polymerase at 37° C. in 0.025 ml mixtures containing: 40 mM Tris-HCl (pH 8.0)/8 mM MgCl$_2$/2 mM spermidine/50 mM NaCl/1 mM each of ATP, CTP, and UTP/5 uM [$\propto$-$^{32}$p]GTP/30 mM dithiothreitol/1 µg of pTFLZ-1 template/40 units of RNasin (Promega Biotech). At various times the reactions were stopped by addition of 0.05 ml of 50 mM EDTA/0.1% SDS/100 µg of proteinase K per ml and incubated for 60 minutes at 37° C. Samples were applied to DE 81 paper (Whatman) and washed three times for 5 minutes in 5% Na$_2$HP0$_4$, once with water and once with 95% ethanol. The samples were dried and counted in a scintillation spectrophotometer.

8.0 β-galactosidase (β-gal) Assay

Approximately $2.5 \times 10^6$ infected or transfected CV-1 cells were suspended in 1 ml of phosphate buffered saline, frozen and thawed three times and dispersed by sonication. The cellular debris was removed by centrifugation and the supernatant was assayed for β-gal activity using o-nitrophenyl-β-D-galactopyranoside as described by Miller, *Experiments in Molecular Genetics*, 1972, pp 352–355. After 30 minutes at 37° C., the reaction was stopped by addition of 1M Ca$_2$C0$_3$ and the yellow color was quantitated at an absorbance of 420 nm. β-gal activity was recorded as nmol of O-nitrophenol produced per $2.5 \times 10^6$ cells.

9.0 Chloramphenicol Acetyltransferase (CAT) Assay

Approximately 2.5×10⁶ infected or transfected CV-1 cells were suspended in 0.2 ml of 0.25M Tris-HCl (pH 7.5). After freezing and thawing three times, the lysates were dispersed by sonication, and the suspension was assayed for enzyme activity as described by Mackett et al. 2., supra.

EXAMPLE II

Construction of Plasmids pGS53 and PGS50

Plasmid pGS53 is basically similar to pGS20 (Mackett, Smith and Moss, *J. Virol.* 49, 857–864) which also could have been used to construct a recombinant vaccinia virus that expresses T7 RNA polymerase gene 1. Unless otherwise indicated, all recombinant DNA steps were carried out by standard procedures such as those previously used for construction of pGS20 and those described by T. Maniatis, E. F. Fritsch and J. Sambrook *Molecular Cloning*, Cold Spring Harbor Laboratory, Cold Spring Harbor, N.Y. 1982. Plasmid pUC13 was cleaved with restriction endonuclease EcoRI, extracted with phenol-chloroform and ethanol precipitated. The linearized plasmid was then digested with nuclease S1 to remove the 5' overhanging nucleotides at the EcoRI site and again phenol-chloroform extracted and ethanol precipitated. To ensure that the DNA ends were blunt, the plasmid was then incubated with all four deoxyribonucleoside triphosphates and the Klenow fragment of DNA polymerase. The DNA was purified once more by phenol-chloroform extraction and ethanol precipitated and ligated to a 1,800 base pair DNA fragment containing the vaccinia virus thymidine kinase gene. The latter 1,800 base pair DNA fragment was produced by digesting the HindIII J fragment of vaccinia virus (New York City Board of Health strain from Wyeth Laboratories) with PvuII and was purified by agarose gel electrophoresis. Transformation competent *E. coli* were transformed with the ligated DNA and transformants were selected and grown and the plasmid designated pGS50 was amplified and purified. pGS50 that had been cleaved with EcoRI and phosphatase treated was ligated to an agarose gel purified fragment of approximately 290 base pairs, that contains the vaccinia virus P7.5 promoter with downstream BamHI and SmaI sites, which was obtained by digesting pGS19 (Mackett, Smith and Moss, *J. Virol.* 29, 857–864) with EcoRI. Transformation competent *E. coli* were transformed with the ligated DNA and transformants were selected and grown and the plasmid designated pGS53 was amplified and purified.

EXAMPLE III

Construction of Recombinant Plasmid pAR2529

Plasmid pAR2529 contains the bacteriophage T7 promoter, Ø10, and terminator, TØ, and was constructed as follows. Synthetic BamHI linkers, CGGGATCCCG, were ligated to a fragment of T7 DNA (nucleotides 22,880–22,928) containing the Ø10 promoter for T7 RNA polymerase digested with BamHI and inserted into the BamHI site of pBR322. The fragment extends from nucleotides −23 to +26 relative to the start of the RNA and is oriented so that transcription from the Ø10 promoter is directed counterclockwise, opposite to transcription from the tetracycline promoter. The upstream BamHI site was converted to a BglII site by partial digestion with BamHI, removal of the 5' overhang by filling in with the Klenow fragment of *E. coli* DNA polymerase in the presence of all four deoxyribonucleotides, adding the linker GAGATCTC, cleaving with BglII, and re-ligating. A fragment of T7 DNA containing TØ (nucleotides 24,106–24,228, where transcription terminates at nucleotide 24,209) was joined to the downstream BamHI cloning site through the sequence GGATCCGG'-T0-CCG-GATCGAGATCTCGATCC, where the final C is nucleotide 375 in the BamHI site of pBR322. The downstream linker contains a BglII site, so the entire Ø10-BamHI-TØ fragment can be removed from this plasmid as a BglII fragment for transfer to other vectors.

EXAMPLE IV

Construction of Plasmid DTF7-3

Plasmid pTF7-3 (A.T.C.C. No. 67202) was constructed by inserting a 2.65 Kb DNA fragment, containing the entire T7 gene 1 coding region for T7 RNA polymerase, into the BamHI site of pGS53.10 µg of plasmid pAR1173 (Davanloo, P., Rosenberg, A. H., Dunn, J. J., and Studier, F. W. (1984) *PNAS USA* 81, 2035–2039.) was digested with BamHI, separated by gel electrophoresis, and the 2.65 Kb T7 RNA polymerase DNA fragment isolated following the Elutip-d (Schleicher and Schuell) method. 5 µg of pGS53 DNA was cleaved with BamHI and gel purified as above. The 2.65 Kb T7 RNA polymerase DNA fragment was ligated to pGS53 and used to transform competent *E. coli* cells following procedures as outlined in Maniatis et al., Molecular Cloning, Cold Spring Harbor Laboratories, Cold Spring Harbor, N.Y., 1982.

EXAMPLE V

Construction of Plasmid pTF7LZ-1

Plasmid pTF7LZ-1 was constructed by inserting an *E. coli* lacZ DNA fragment containing a translation initiation codon, ATG, inframe with the lacZ coding sequence into the BamHI site of pAR2529. The lacZ DNA fragment was isolated from the plasmid pWS61 (obtained from Alokes Maoumdar, NIH, unpublished) as a 3.2 Kb XbaI/Aha3 fragment which contains the following DNA sequence upstream from the 9th codon of the lacZ structural gene: TCTAGATTATTTGCATACATTCAAT-CAATTGTTATCTAAGGAAATACTT ACATATGGT-TCGTGCTAACAAACGCAACGAGGCT CTAC-GAATCGCGATAAGCTAGCTTGGGGGGATCCC.

The 5' overhangs of the 3.2 Kb XbaI/Aha3 fragment were filled in with the Klenow fragment of *E. coli* DNA polymerase in the presence of all four deoxyribonucleotides. Plasmid vector pUC18 was cleaved with BamHI, the 5' overhangs filled in as before, and the blunt-ended lacZ fragment inserted by ligation following standard cloning techniques (Maniatis et al., 1982). The resulting plasmid was named pGa12. 10 µg of pGa12 DNA was digested with XbaI, 5' overhang filled in with the Klenow fragment, cleaved with SmaI, and separated by agarose gel electrophoresis. The 3.2 Kb lacZ fragment was isolated by the Elutip-d method. 10 µg of plasmid pAR2529 DNA was digested with BamHI, made blunt with the Klenow fragment, 5' terminal phosphates removed by treatment with calf intestine alkaline phosphatase, phenol/chloroform extracted once blunt end-ligated to the lacZ fragment, and aliquots of the ligation mixture were used to transform competent *E. coli* HB101 cells following standard techniques. Plasmid clones with lacZ coding sequence in the positive (productive) orientation with respect to the T7 promoter, Ø10, were des ignated pTF7LZ-1.

EXAMPLE VI

Construction of Plasmid pTF7CAT-1

Plasmid pTF7CAT-1 was constructed by inserting a DNA fragment containing the CAT-coding sequence derived from pBR328 into the BamHI site of pAR2529. The CAT gene was isolated as a 770-bp TaqI DNA fragment containing the CAT coding sequence separated from its endogenous start site from pSR328 and cloned into the AccI site of pUC7. Since pUC7 contains BamHI sites closely flanking the AccI sites, the CAT gene was excised with BamHI and inserted into pGS20. (Mackett, M., Smith, G. L., and Moss, B. PNAS USA 49:857–864.). The resulting plasmid was designated pGS30. 10 µg of pGS30 DNA was digested with BamHI and separated by agarose gel electrophoresis. The 0.8 Kb CAT fragment was isolated using the Elutip-d method. 10 µg of pAR2529 DNA was digested with BamHI, 5' terminal phosphates removed by using calf intestine alkaline phosphatase, phenol/chloroform extracted once, ligated to the CAT gene fragment, and aliquots of the ligation mixture used to transform competent E. coli HB101 cells following standard techniques. Plasmid clones with the CAT coding sequence in the positive orientation with respect to the T7 promoter, Ø10, were designated pTF7CAT-1.

EXAMPLE VII

Construction of Plasmid DTF7HB-1

Plasmid pTF7HB-1 was constructed by inserting a DNA fragment containing the coding sequence for hepatitis B surface antigen (HBsAg) gene into the BamHI site of pAR2529. HBsAg coding gene sequence was isolated as a 0.9 Kb BamHI DNA fragment from pHBs4 (Smith, G. L., Mackett, M., and Moss, B. Nature 302: 490–495, 1983). 10 µg of phBs4 DNA was digested with BamHI and the DNA fragments separated by agarose gel electrophoresis. The 0.9 Kb HBsAg fragment was isolated using the Elutip-d method. 10 µg of pAR2529 DNA was digested with BamHI, 5' terminal phosphates removed by calf intestine alkaline phosphatase treatment, phenol/chloroform extracted once, ligated to the HBsAg gene fragment, and aliquots of the ligation mixture used to transform competent E. coli cells following standard techniques. Plasmid clones with the HBsAg coding sequence in the positive orientation with respect to the T7 promoter, Ø10, were designated pTF7HB-1.

EXAMPLE VIII

Construction of Plasmid DTF7ILZ-1

Plasmid pTF7ILZ-1 was constructed by inserting a 3.4 Kb DNA fragment, containing the T7-promoter-lacZ gene T7 terminator BglII fragment from pTF7LZ-1, into the ClaI/EcoRI site of pGS50. 10 µg of pTF7LZ-1 was digested with BglII, 5' protruding ends filled in with the Klenow fragment of E. coli DNA polymerase in the presence of all four deoxyribonucleotides, DNA fragments separated by agarose gel electrophoresis, and the 3.4 Kb fragment isolated by the Elutip-d method. 10 µg of plasmid pGS50 was digested with EcoRI, 5' protruding ends filled in with the Klenow fragment, cleaved with ClaI, treated with calf intestine alkaline phosphatase, and phenol/chloroform extracted. The 3.4 Kb T7 promoter-lacZ gene-T7 terminator fragment was ligated to this preparation of pGS50 and aliquots of the ligation mixture used to transform competent E. coli cells following standard techniques. Plasmid clones with the lacZ coding sequence in the same orientation as the thymidine kinase (TK) coding sequence were designated pTF71LZ-1.

EXAMPLE IX

Construction of Plasmid pTF7IHB-1

Plasmid pTF7IHB-1 was constructed by inserting a 1.1 Kb DNA fragment, containing the T7 promoter-HBsAg gene-T7 terminator BglII fragment from pTF7HB-1, into the ClaI/EcoRI site of pGS50. 10 µg of pTF7HB-1 was digested with BglII, the 5' protruding ends filled in using the Klenow fragment, DNA fragments separated by agarose gel electrophoresis, and the 1.1 Kb fragment purified using the Elutip-d method. 10 µg of pGS50 DNA was cleaved with EcoRI, 5' protruding ends filled in with the Klenow fragment, digested with ClaI, treated with calf intestine alkaline phosphatase, and phenol/chloroform extracted. The 1.1 Kb DNA fragment was ligated to the preparation of pGS50 and aliquots of the ligation mixture were used to transform competent E. coli cells. Plasmid clones with the coding sequence of HBsAg in the same orientation as the TK coding sequence were designated pTF71HB-1.

EXAMPLE X

Construction of Recombinant Virus vTF7-3

Construction of the recombinant virus, vTF7-3 (A.T.C.C. No. VR 2153) was done using the following procedures. CV-1 cells were infected with 0.05 plaque forming units (PFU) per cell of wild-type vaccinia virus and transfected with calcium phosphate-precipitated pTF7-3 DNA following procedures described previously (Mackett, M., Smith, G. L., and Moss, DNA Cloning, Vol. 2, ed Glover, D. M. IRL Press, Oxford, pp. 191–211 1985). Recombinant virus was formed by homologous recombination into the TK locus and TK⁻ virus was selected by plaque assay on TK⁻ 143 cell monolayers in the presence of BUdR (25 ug per ml). TK- recombinant virus plaques were distinguished from spontaneous TK⁻ mutant virus by DNA:DNA dot blot hybridization (ibid). After two consecutive plaque purifications the recombinant virus, vTF7-3, was amplified by infecting TK-143 cell monolayers in the presence of BUdR and then large stocks were made in HeLa cells without selection.

EXAMPLE XI

Construction of Recombinant Viruses vTF7LZ-1 and vTF7HB-1

Recombinant viruses vTF7LZ-1 (A.T.C.C. No. VR 2152) and vTF7HB-1 (A.T.C.C. No. VR 2154) were constructed following the same procedures as outlined above using plasmid vectors pTF71LZ-1 and pTF71HB-1, respectively.

EXAMPLE XII

Construction of Recombinant Vaccinia Virus Containing a Chimeric Bacteriophage T7 RNA Polymerase Gene Procedures for the insertion and expression of foreign genes in vaccinia virus have been described in detail, Mackett et al., 1 and 2, supra. Vaccinia virus promoters are required to regulate transcription of the DNA which is introduced by homologous recombination into the 185,000 bp linear double-stranded DNA genome. To facilitate the use of vaccinia virus as a vector, a series of plasmids were made that contain a vaccinia virus promoter, restriction endonuclease sites for insertion of foreign DNA, and flanking vaccinia TK (thymidine kinase) sequences to direct recombination into the TK locus of the genome. For this study we used the plasmid pGS53 which contains a promoter termed P7.5 with early and late regulatory signs as described by Cochran et al., *J. Virology* 1985, 53, pp 30–37) to permit continuous expression of foreign genes. A 2.65 kilobase pair (Kb) DNA fragment, containing the entire T7 gene 1 coding region for T7 RNA polymerase, was excised with BamHI from plasmid pAR1173 described by Davanloo et al., *Proc. Nat. Acad.*, 1984, 81, pp 2035–2039, and inserted into the unique BamHI site of pGS53 as shown in FIG. 1. A plasmid designated pTF7-3, with the vaccinia promoter and T7 RNA polymerase in proper orientation, was isolated from transformed *E. coli.* Plasmid pTF7-3 was used to transfect cells that were infected with vaccinia virus and then TK⁻ recombinant virus plaques were selected. Correct insertion of the T7 RNA polymerase gene into the genome of vTF7-3 was confirmed by DNA blot hybridization.

EXAMPLE XIII

Expression of T7 RNA Polymerase in Mammalian Cells

Figure 2:
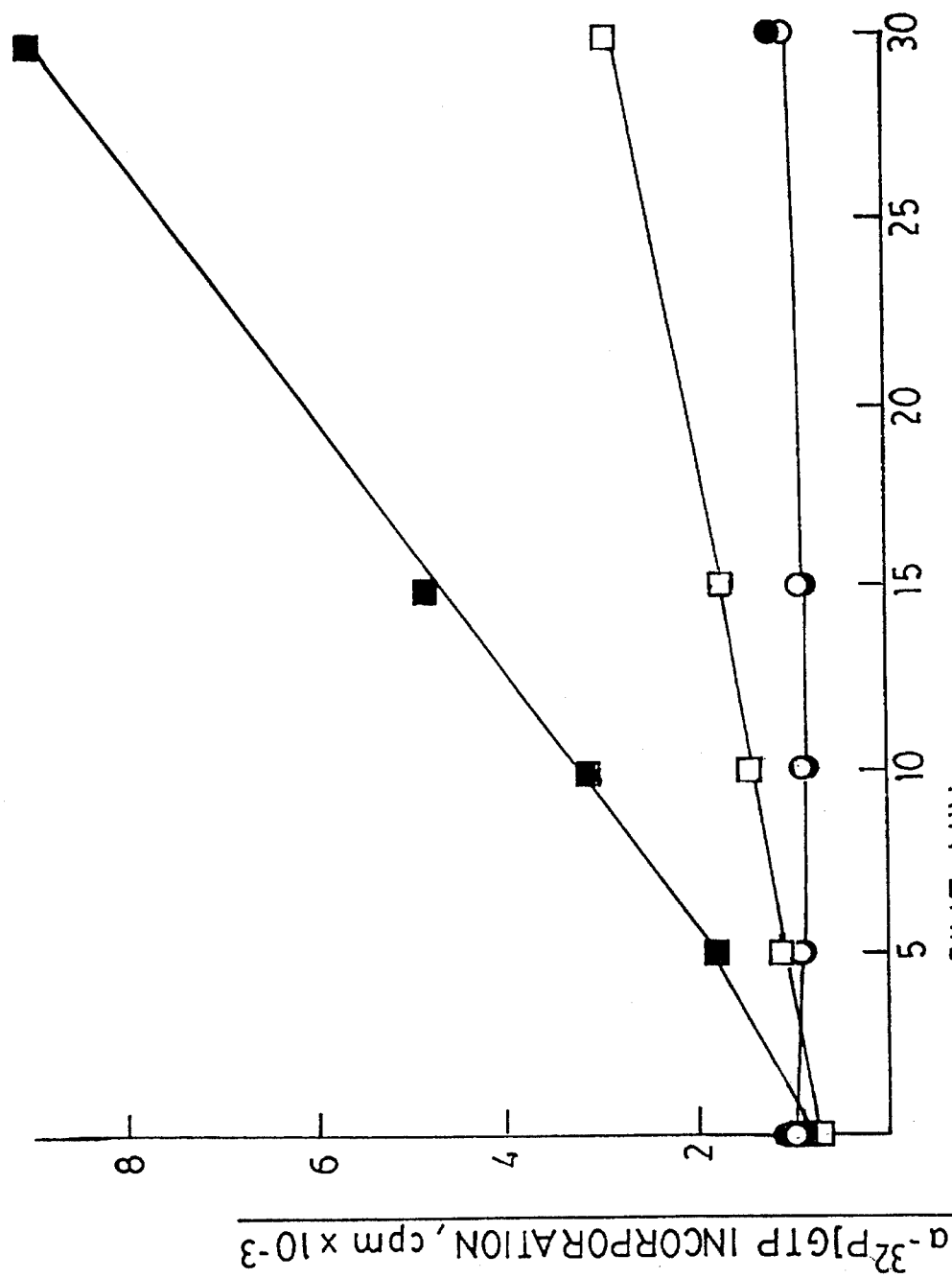
FIG. 2 is a graph demonstrating the synthesis of T7 RNA polymerase. Extracts were prepared from uninfected cells O, cells infected with vaccinia virus ●, infected with vaccinia virus and transfected with pTF7-3 □, or infected with vTF7-3 ■ and assayed for T7 RNA polymerase. Incorporation of [$\alpha$-$^{32}p$]) GTP into RNA that bound to DEAE-cellulose filters was measured.

Previous studies, Cochran et al., 1., supra, indicated that plasmids containing genes under control of a vaccinia virus promoter are specifically transcribed in cells infected with vaccinia virus. To determine whether active T7 RNA polymerase would be synthesized when vaccinia virus infected cells were transfected with the plasmid pTF7-3, T7 RIgA polymerase activity in cell lysates was assayed using a DNA template containing a T7 promoter. Initial experiments established that RNA polymerase activity measured with this template was not increased after vaccinia virus infection alone, as shown in FIG. 2. When vaccinia virus infected cells were also transfected with pTF7-3, however, a significant increase in activity was observed (FIG. 2). Additional experiments demonstrated that T7 RNA polymerase activity was not detected when uninfected cells were transfected with pF7-3 or when infected cells were transfected with a plasmid containing the T7 gene 1 without a vaccinia promoter.

To demonstrate whether higher levels of T7 RNA polymerase would be expressed when the T7 gene 1 under control of a vaccinia promoter was integrated into the vaccinia virus genome the following procedures were followed. As shown in FIG. 2, vTF7-3 infected cell extracts contained several times more T7 RNA polymerase activity than was present in cells that had been transfected with pTF7-3 in the presence of wild-type vaccinia virus. This quantitative difference between recombinant virus and transient expression systems was consistent with previous observations.

EXAMPLE XIV

Construction of Plasmids Containing Target Genes with T7 Promoters

Figure 3:
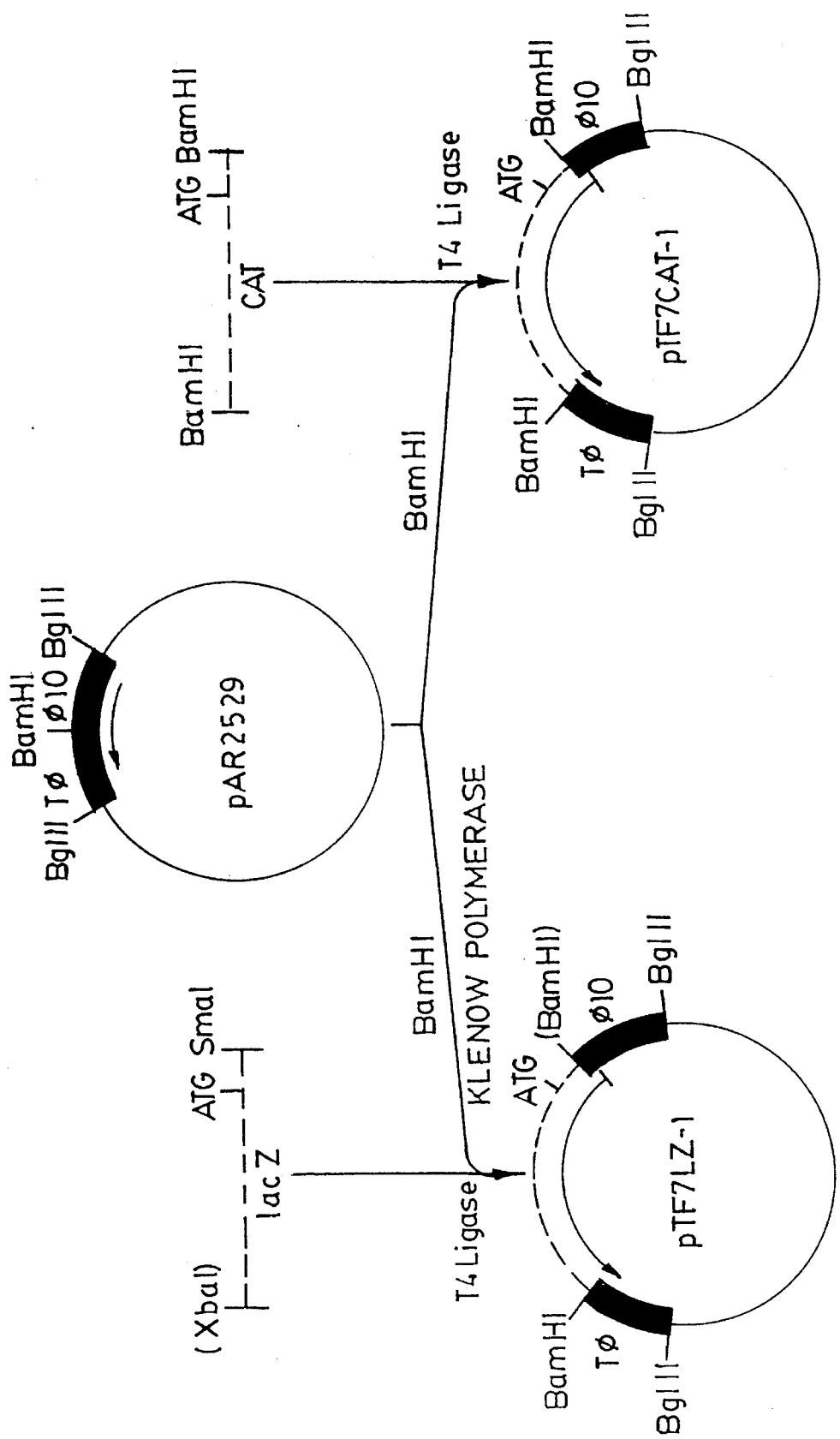
FIG. 3 is a schematic diagram showing construction of plasmids containing target genes flanked by T7 promoter and terminator sequences. A 3.2 Kb DNA segment containing the lacZ gene with translation and termination codons was obtained by cleavage of pWS61 (provided by A. Majmdar, NIH) with XbaI, filling in the staggered end with the Klenow fragment of DNA polymerase and deexynucleoside triphosphates, and cleaving with SmaI. The fragment was then blunt-end ligated to pAR2529 which had been cleaved with BamHI and treated with Klenow fragment of DNA polymerase. The resulting plasmid, pTF7LZ-1 has the coding sequence for β-gal flanked by the T7 Ø 10 promoter and TØ terminator. Similarly, a 0.7 Kb BamHI fragment from pGS30 containing the CAT gene was ligated to BamHI cleaved pAR2529 to form pTF7CAT-1.

To determine whether bacteriophage T7 RNA polymerase made under control of vaccinia virus can function in mammalian cells, we constructed plasmids containing target genes flanked by T7 promoter and termination regulatory elements. Plasmid pAR2529 (A. H. Rosenberg, J. J. Dunn and F. W. Studlet) contains the ⌀10 promoter separated by a unique BamHI site from the T7 terminator T⌀, which has a potential stem-loop structure followed by a run of thymidylate residues. As targets, we chose the *E. coli* β-gal gene (called lacZ) and the CAT gene derived from the TN9 transposon. These genes are ideal for expression systems because simple and quantitative assays are available for the enzyme products and there is no detectable background activity in mammalian cells. The lacZ or CAT gene, each with an associated ATG translation initiation codon, was inserted into the unique BamHI site of pAR2529, as shown in FIG. 3. Plasmids with lacZ and CAT in the correct orientation were designated pTF7LZ-1 and pTF7CAT-1, respectively.

EXAMPLE XV

Transient Expression of β-gal

Previously, cells infected with vaccinia virus and transfected with a plasmid containing the T7 gene 1 under control of a vaccinia virus promoter synthesized T7 RNA polymerase were discussed. It was further determined that vaccinia virus infected cells would express β-gal if they were transfected with plasmids containing the T7 gene 1 under control of a vaccinia promoter and the lacZ gene under control of a T7 promoter. Transient expression depends on vaccinia virus regulated synthesis of T7 RNA polymerase, the intracellular functioning of the T7 RNA polymerase, the production of translatable m-RNA from a T7 promoter, and the synthesis of a prokaryotic enzyme. As shown in Table 1, β-gal was detected in cell lysates. Omission of either vaccinia virus or the plasmid containing the T7 RNA polymerase gene prevented expression of β-gal. Negative results also were obtained when, either the T7 gene 1 or lacZ gene was oriented oppositely with respect to the vaccinia or T7 promoter, respectively.

In both experiments above, the T7 gene 1 and the lacZ gene were transcribed from plasmids. Since more T7 RNA polymerase is made when gene 1 is integrated into vaccinia virus, as shown in FIG. 2, higher amounts of β-gal are produced if cells are infected with recombinant vaccinia virus vTF7-3 and then transfected with the lacZ plasmid pTFLZ-1. As shown in Table 1, more than twice as much β-gal was made when T7 RNA polymerase was expressed by a recombinant virus than from a plasmid.

The expression of β-gal under control of T7 and vaccinia virus promoters was further determined. The vaccinia virus promoter used, P7.5, was the same as that regulating expression of T7 gene 1. When cells were infected with vaccinia virus and transfected with the plasmid containing the β-gal gene under control of the vaccinia promoter, β-gal activity was about 5% of that obtained with the vaccinia/T7 transient system. In fact, the level of β-gal obtained with the vaccinia/T7 transient system was higher than that obtained even when the β-gal gene with the P7.5 promoter was inserted into the vaccinia virus genome and the recombinant virus was used to infect cells as shown in Table 1. In these experiments, substantial amounts β-gal were made without changing the pyrimidine, at the −3 position relative to the translation initiation codon, to a purine so as to fit the eukaryotic consensus sequence shown by Kozak, *Nucleic Acids Res.*, 12, pp 3873–3893).

EXAMPLE XVI

Transient Expression of CAT

It is important to compare the vaccinia/T7 transient expression system of the present invention with a more conventional system which is used in mammalian cells.

Since CAT is the most common target gene used in mammalian cells for comparison of expression levels, experiments similar to those performed with β-gal were repeated and are shown in Table 1. As in the case of β-gal, it was observed that transient expression of CAT from the T7 promoter was higher when the T7 gene 1 was integrated into vaccinia virus than when it was co-transfected on a second plasmid. Also, expression was observed to be much higher in the vaccinia virus/T7 hybrid system of the present invention in comparison to when the CAT gene was expressed directly from the vaccinia promoter.

Figure 4:
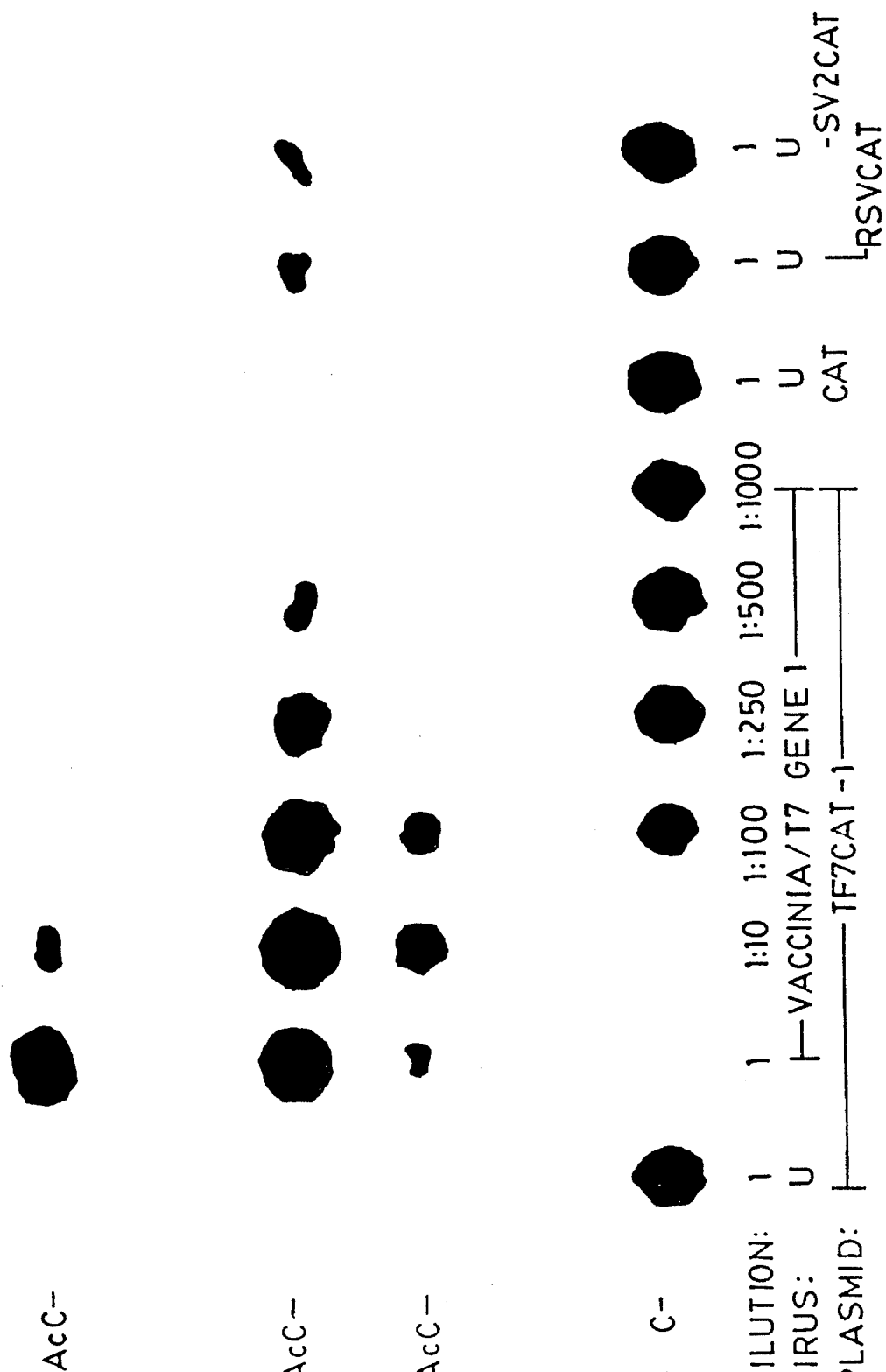
FIG. 4 shows a comparison of transient expression systems. Cell lysates were prepared at 48 hr after infection with vTF7-3 (vaccinia/T7 gene 1) and/or transfection with the indicated plasmid and assayed for CAT. Samples were spotted on a silica gel plate and chromotographed. An autoradiograph is shown with the positions of chloramphenicol (C) and acetylated forms of chloramphenicol (AcC) indicated.

For further comparison, CV-1 cells were transfected with pSV2CAT or pRSVCAT which contain the same CAT DNA fragment derived from the TN9 transposon as pTF7CAT-1 and either the enhancer and promoter from the Rous sarcoma virus (RSV) long terminal repeat or the simian virus 40 (SV40) early region. In order not to prejudice the results in favor of the vaccinia/T7 system, previously described experimental conditions for expression of pSV2CAT and pRSVCAT were employed. Thus, low passage CV-1 cells and glycerol boosting were used and cell lysates were made at 48 hours after transfection. The extracts were diluted and tested for CAT activity. As shown in the autoradiogram in FIG. 4, several hundred times more CAT was made in the vaccinia/T7 system than with either pSV2CAT or pRSV-CAT. More quantitative results obtained by scintillation counting indicated that 4560 nmol of chloramphenicol were acetylated per $2.5 \times 10^6$ cells using the vaccinia/T7 system compared to only 6.8 with pSV2CAT or 9.1 with pRSVCAT. This difference was even greater when glycerol boosting was omitted and cells were lysed at 24 hours after transfection.

respectively. Target genes lacZ and HBsAg were flanked by T7 promoter and terminator sequences. These chimeric fragments were shuttled as cassettes and inserted into the TK DNA sequence of pGS50. The resulting recombinant viruses, vTF7LZ-1 and vTF7IHB-1, now contain target genes lacZ and HBsAg, respectively, under the control of T7 promoter.

Furthermore, co-infection of cultured mammalian cells by recombinant vaccina virus that produces T7 RNA polymerase (vTF7-3) and either vTF7LZ-1 or vTF7HB-1 results in specific high-level expression of β-gal or HBsAg. Comparison of vaccinia/T7 mixed infection expression levels to those previously obtained with recombinant vaccinia viruses is shown in Table 2. Expression with the vaccinia/T7 β-gal is approximately 5-fold higher than with a vaccinia recombinant containing lacZ under the control of the vaccinia virus P7.5 promoter inserted in the TK locus. The level of HBsAg production using the vaccinia/T7 system is also higher than the corresponding single vaccinia recombinant. CV-1 cells were infected or co-infected with recombinant (T7 gene 1, lacZ, or HBsAg) vaccinia virus(es) at a multiplicity of 10 PFU of virus per cell. The recombinant viruses had the foreign gene under control of either the vaccinia virus P7.5 promoter (VV) or the T7 promoter and inserted into the TK locus. Cells were harvested after 24 hours and cell lysates and media were assayed for β-gal or HBsAg. Expression of β-gal is given as total nmol of product formed in 30 minutes per $2.5 \times 10^6$ cells. Expression for HBsAg is given as total $CPM \times 10^3$ obtained from a radio-radioimmunoassay immunoassay (AUSRUA II, Abbott) per $2.5 \times 10^6$ cells. Accordingly, the novel system of the present invention directs high-level expression of target genes.

TABLE 1

Transient Expression of β-gal and CAT

| Virus | Plasmid 1 | | Plasmid 2 | | Expression | |
|---|---|---|---|---|---|---|
| Vaccinia | Promoter | Gene | Promoter | Gene | β-gal | CAT |
| WT | VV | T7 1 | T7 | lacz | 1100 | |
| | VV | T7 1 | T7 | lacz | 0 | |
| WT | | | T7 | lacz | 0 | |
| T7 gene 1 | | | T7 | lacz | 2406 | |
| WT | | | VV | lacz | 137 | |
| lacZ | | | | | 480 | |
| WT | VV | T7 1 | T7 | CAT | | 1650 |
| | VV | T7 1 | T7 | CAT | | 0 |
| WT | | | T7 | CAT | | 0 |
| T7 gene 1 | | | T7 | CAT | | 4330 |
| WT | | | VV | CAT | | 300 |
| CAT | | | | | | 1430 |

CV-1 cells were uninfected or infected with wild-type (WT) or recombinant (T7 gene 1, lacZ, or CAT) vaccinia virus. The recombinant viruses had the foreign gene under control of the vaccinia virus P7.5 promoter and inserted into the TK locus. Uninfected or infected cells were transfected with 1 or 2 plasmids containing either the T7 gene 1, β-gal gene or CAT gene under control of the vaccinia virus P7.5 promoter (VV) or the T7 010 promoter. Cells were harvested after 24 hours and lysates were assayed for β-gal or CAT. Expression is given as nmol of product formed in 30 minutes per $2 \times 10^6$ cells.

Figure 5:
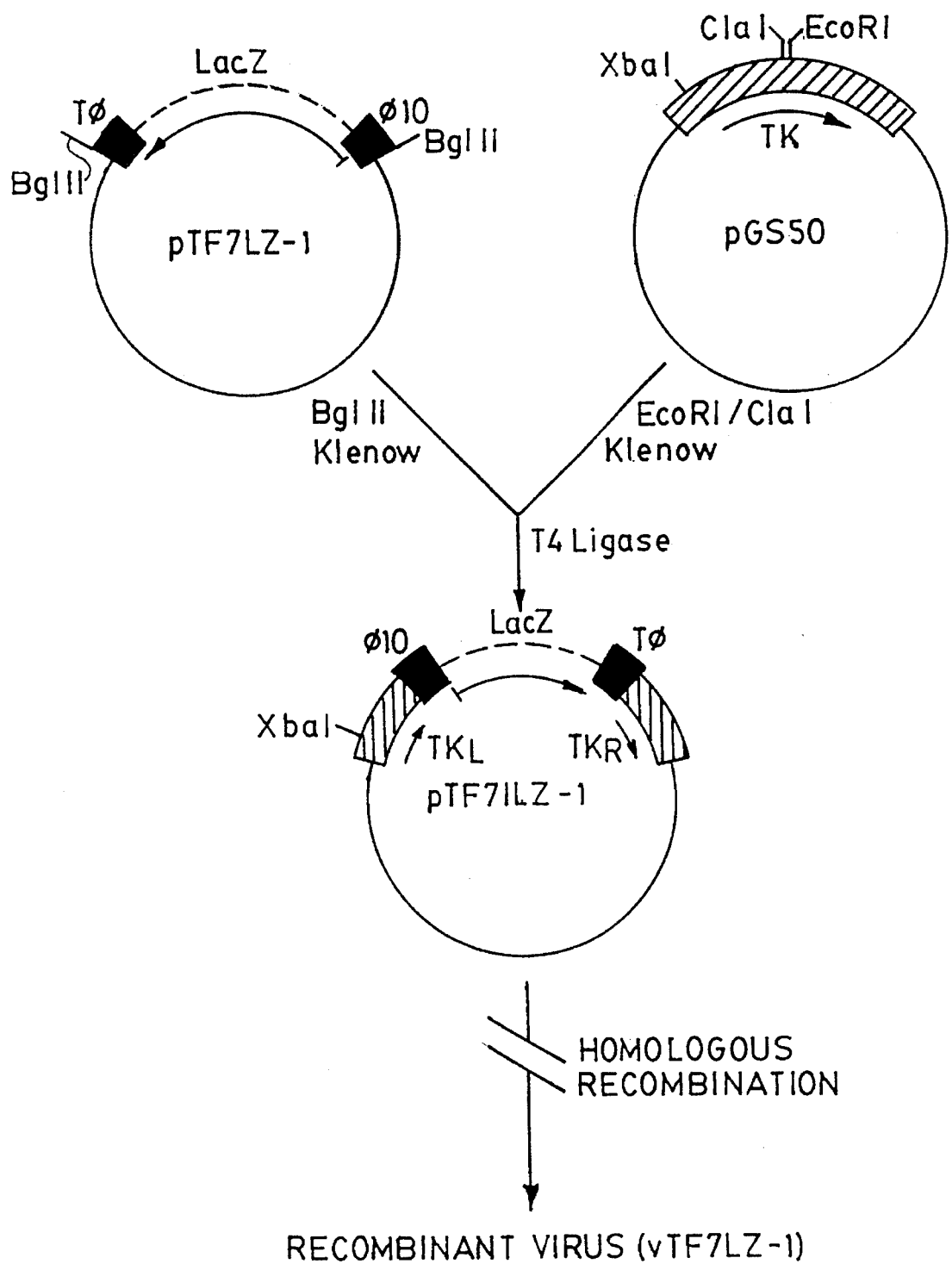
FIG. 5 shows the construction of plasmid pTFILZ-1 and recombinant vaccinia virus vTF7LZ-1 containing the chimeric target gene for E. coli β-galactosidase (lacZ).
Figure 6:
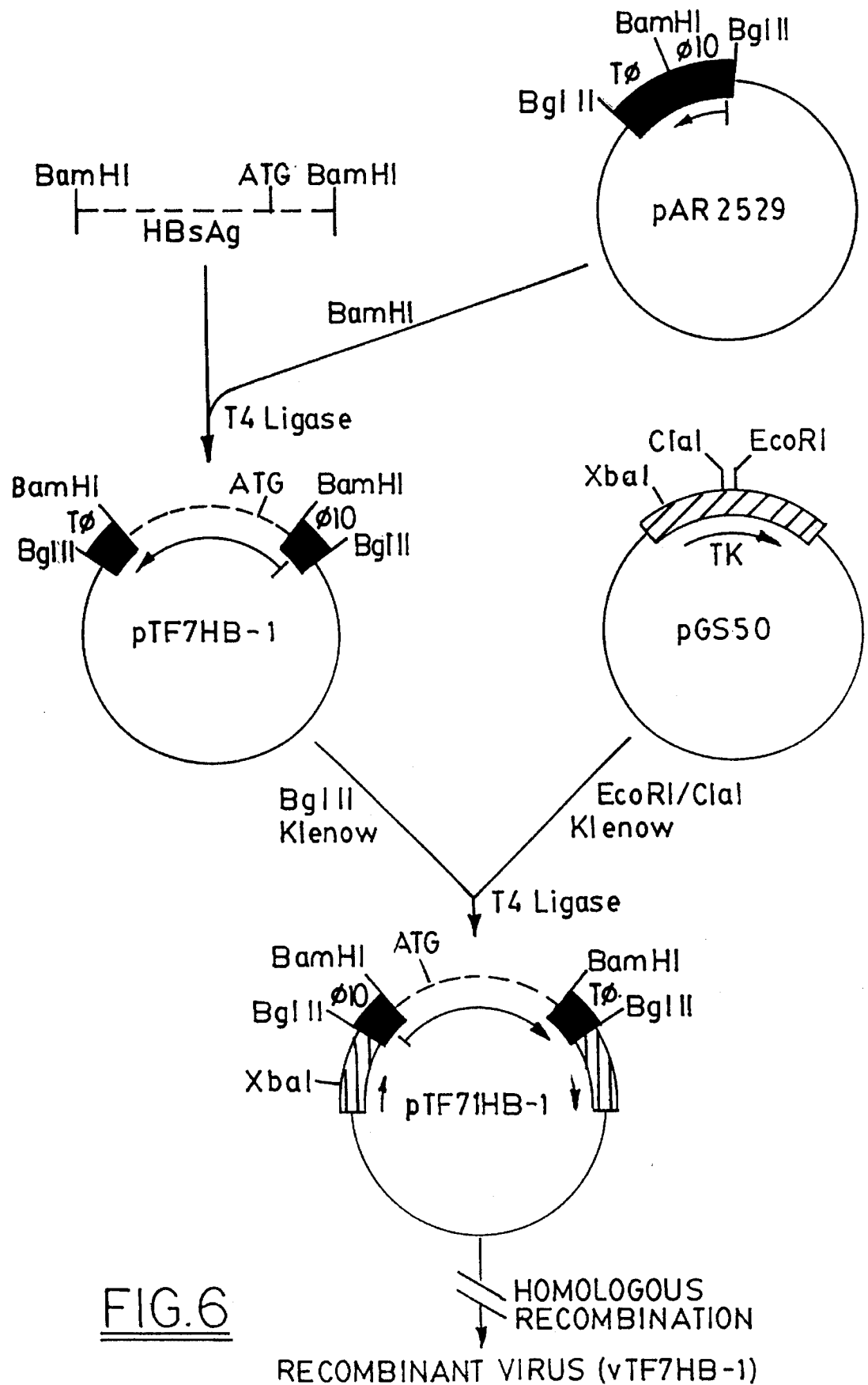
FIG. 6 shows recombinant vacciniavirus vTF7HB-1 containing the hepatitis B virus HBsAg gene.

Utility of the present system is further shown by demonstrating that higher levels of expression can be obtained by incorporating the chimetic target gene into vaccinia virus. Construction of recombinant viruses containing the chimetic target genes for *E. coli* β-galactosidase (lacZ), and hepatitis B surface antigen (HBsAG) is shown in FIGS. 5 and 6,

TABLE 2

Mixed Infection Expression of β-gal and HBsAg

| Virus 1 | | Virus 2 | | Expression | |
|---|---|---|---|---|---|
| Promoter | Gene | Promoter | Gene | β-gal | HBsAg |
| VV | T71 | | | 0 | 0 |
| T7 | lacz | | | 0 | |
| VV | T7 1 | T7 | lacz | 62,000 | |
| VV | lacz | | | 12,000 | |
| T7 | HBs | | | | 0 |
| VV | T71 | T7 | HBs | | 1225 |
| VV | HBs | | | | 800 |

Expression of eukaryotic genes in prokaryotes and vice versa is known in the art. However, this generally involves only exchanges in coding sequences. The transfer of a transcription system from a prokaryote to a eukaryote, as disclosed in the present invention, opens up new opportunities for regulating gene expression. The present invention has accomplished integration of a gene which encodes a functional bacteriophage RNA polymerase into a virus with specificity for eukaryotic cells by utilizing a single subunit RNA polymerase characterized by stringent promoter specificity, and cytoplasmic DNA virus that encodes its own RNA modifying enzymes.

Transcription of the T7 RNA polymerase gene in vaccinia virus infected cells is accomplished by the vaccinia RNA polymerase and therefore is dependent on the fusion of the bacteriophage gene to a vaccinia promoter. Expression of T7 RNA polymerase could be obtained either by transfecting vacinia virus infected cells with a plasmid containing the chimeric gene or by integrating the gene into a nonessential site within the genome of the vaccinia virus. Recombinant viruses were stable, could be grown to high titer and produced higher levels of T7 RNA polymerase than cells transfected with the plasmids.

The target genes chosen for expression by T7 RNA polymerase were cloned into the plasmid at a unique restriction site separating a T7 promoter from a T7 terminator. For these studies, the target genes (lacZ and CAT) had associated translational initiation codons, but other plasmid vectors that supply the ATG and appropriate flanking nucleotides could be used for production of fusion proteins. The key step was to transfect these plasmids into cells that were infected with the vaccinia virus recombinant which expressed the T7 RNA polymerase gene. The synthesis of β-gal and CAT was compared by the vaccinia/T7 expression system of the present invention to that which occurred with a straight vaccinia transient expression system (in which the target gene has a vaccinia promoter) and to a conventional transient expression system (in which either the enhancer and promoter from the long terminal repeat of Rous sarcoma virus or the early region of SV40 were used). The vaccinia/T7 system was 15 to 20 fold more efficient than the straight vaccinia system and 400 to 600 fold more efficient than the conventional system.

The greater efficiency of the vaccinia/T7 transient system of the present invention when compared to that of more conventional system may be attributed to several factors. First, since it is possible to infect tissue culture cells synchronously with vaccinia virus, all cells may have T7 RNA polymerase. Moreover, T7 RNA polymerase is a very active enzyme with a 5 fold faster elongation rate than that of *E. coli* RNA polymerase. It would appear that the bacteriophage enzyme is able to function within the eukaryotic environment. In addition, since the vaccinia virus RNA modifying enzymes and presumably T7 RNA polymerase are localized in the cytoplasm, the transfected plasmid does not have to enter the nucleus for transcription and the mRNA produced does not have to be processed and transported back to the cytoplasm for translation.

Current knowledge in the field of vaccinia virus expression vectors should be directly applicable to the expression system of the present invention. For example, there is abundant evidence that eukaryotic proteins made in vaccinia virus infected cells are properly processed, glycosylated, and transported to the plasma membrane. In addition, because of the wide host range of vaccinia virus, a variety of vertebrate cells of mammalian and avian origin are suitable. The T7 promoter is especially versatile because of its use for in-vitro synthesis of translatable mRNA and in prokaryotic expression vectors. Development of the vaccinia/T7 hybrid virus system makes it possible to use previous or slightly modified plasmid vectors for a third purpose: efficient expression of genes in eukaryotic cells. We have concentrated our initial efforts on the application of the vaccinia/T7 system for transient expression of target genes in plasmids because of its simplicity and potentially wide application in this configuration. However, even higher levels of expression may be possible when both the T7 RNA polymerase gene and the target gene are carried by vaccinia virus vectors.

It is to be understood that the invention is by no means limited to the specific examples which have been illustrated and described herein and that various modifications thereof that may suggest themselves to one of ordinary skill in the art are within the scope of the present invention as defined by the appended claims.

We claim:

1. A method of expressing a gene in a eukaryotic cell comprising incorporating into said cell:

a DNA-based cytoplasmic virus;

a first carrier including a first gene encoding a bacteriophage RNA polymerase selected from the group consisting of T7, SP6, GH1 and T3 RNA polymerase, said first gene being foreign to the carrier and to the cell, and a first promoter sequence which initiates expression of said first gene; and a second carrier comprising a functional cistron comprising a second foreign gene including a second promoter sequence responsive to said bacteriophage RNA polymerase, such that upon recognition of said RNA polymerase, said second promoter initiates expression of the second foreign gene in the eukaryotic cell.

2. The method of claim 1, wherein said virus is selected from the group consisting of poxvirus and iridovirus.

3. The method of claim 2, wherein said virus is poxvirus.

4. The method of claim 3, wherein said poxvirus is selected from the group consisting of orthopoxvirus, parapoxvirus, avipoxvirus, capripoxvirus, leporipoxvirus, suipoxvirus, molluscipoxvirus and yatapoxvirus.

5. The method of claim 4, wherein said poxvirus is orthopoxvirus.

6. The method of claim 5, wherein said orthopoxvirus is vaccinia.

7. The method of claim 1, wherein said first carrier is a plasmid.

8. The method of claim 7, wherein said first promoter is a poxvirus promoter.

9. The method of claim 8, wherein said first gene is the T7 RNA polymerase gene.

10. The method of claim 9, wherein said plasmid is pTF7-3 having A.T.C.C. Designation Number 67202.

11. The method of claim 1, wherein said second carrier is a plasmid.

12. The method of claim 1, wherein said second promoter is a T7 promoter.

13. The method of claim 11, wherein said second foreign gene is a eukaryotic gene.

14. The method of claim 11, wherein said cistron further includes a terminator sequence.

15. A method of expressing a gene in a eukaryotic cell comprising incorporating into said cell:

a DNA-based cytoplasmic virus including a first gene encoding a bacteriophage RNA polymerase selected from the group consisting of T7, SP6, GH1 and T3 RNA polymerase, which first gene is foreign to the virus and to the cell, and a first promoter sequence which initiates expression of the first gene; and a carrier comprising a functional cistron comprising a second foreign gene including a second promoter sequence responsive to said bacteriophage RNA polymerase, such that upon recognition of said RNA polymerase, said second promoter initiates expression of the second foreign gene in the eukaryotic cell.

16. The method of claim 15, wherein said virus is poxvirus.

17. The method of claim 16, wherein said poxvirus is vaccinia.

18. The method of claim 15, wherein said virus is vTF7-3 having A.T.C.C. Designation Number VR 2153.

19. The method of claim 15, wherein said carrier is a DNA-based cytoplasmic virus.

20. The method of claim 19, wherein said first gene is the T7 RNA polymerase gene.

21. The method of claim 15, wherein said second promoter is a T7 promoter.

22. The method of claim 15, wherein said carrier is a plasmid.

23. The method of claim 22, wherein said plasmid is pTF7CAT-1.

24. The method of claim 22, wherein said virus is poxvirus.

25. The method of claim 24, wherein said poxvirus is vaccinia.

26. The method of claim 22, wherein said plasmid is PTF7LZ-1.

27. The method of claim 19, wherein said carrier is vTF7LZ-1 having A.T.C.C. Designation Number VR 2152.

28. The method of claim 19, wherein said carrier is vTF7HB-1 having A.T.C.C. Designation Number VR 2154.

29. The method of claim 22, wherein said second foreign gene encodes HBsAg.

30. The method of claim 29, wherein said second promoter is a T7 promoter.

31. The method of claim 29, wherein said second foreign gene is lacZ.

32. The method of claim 29, wherein said second foreign gene is CAT.

33. A eukaryotic cell capable of expressing a foreign gene in the cytoplasm of the cell, comprising incorporated into said cell:

a DNA-based cytoplasmic virus including a first gene encoding a bacteriophage RNA polymerase selected from the group consisting of T7, SP6, GH1 and T3 RNA polymerase, said first gene being foreign to the virus and to the cell, and a first promoter sequence which initiates expression of said first gene; and a carrier comprising a functional cistron comprising a second foreign gene including a second promoter sequence responsive to said bacteriophage RNA polymerase, such that upon recognition of said RNA polymerase, said second promoter initiates expression of the second foreign gene in the eukaryotic cell.

34. The cell of claim 33, wherein said virus is vaccinia.

35. The cell of claim 33, wherein said first gene is the T7 RNA polymerase gene.

36. The cell of claim 33, wherein said carrier is a plasmid.

37. The cell of claim 33, wherein said second promoter is a T7 promoter.

38. The cell of claim 33, wherein said cistron further includes a terminator sequence.

39. The cell of claim 33, wherein said carrier is a DNA-based cytoplasmic virus.

40. The cell of claim 39, wherein said carrier is vaccina.

41. The cell of claim 39, wherein said second promoter is a T7 promoter.

42. The cell of claim 39, wherein said cistron further includes a terminator sequence.

43. A DNA-based cytoplasmic virus containing a foreign gene encoding a bacteriophage RNA polymerase selected from the group consisting of T7, SP6, GH1 and T3 RNA polymerase.

* * * * *

UNITED STATES PATENT AND TRADEMARK OFFICE
CERTIFICATE OF CORRECTION

PATENT NO. : 5,550,035
DATED     : August 27, 1996
INVENTOR(S) : Moss, et. al.

It is certified that error appears in the above-indentified patent and that said Letters Patent is hereby corrected as shown below:

Title page, item [73] Assignee, the following text should be added: --; Government of the United States of America Secretary, Department of Health and Human Services, Rockville, M.D.--

Signed and Sealed this

Eleventh Day of February, 1997

Attest:

BRUCE LEHMAN

Attesting Officer     Commissioner of Patents and Trademarks